United States Patent
Aita et al.

(10) Patent No.: US 6,267,757 B1
(45) Date of Patent: *Jul. 31, 2001

(54) REVASCULARIZATION WITH RF ABLATION

(75) Inventors: Michael Aita, Shorewood, CA (US); Daniel Burkhoff, Tenafly, NJ (US); Noriyoshi Yamamoto, Okayama (JP); Miriam H. Taimisto, San Jose, CA (US); Kenneth P. Aron, Burlingame, CA (US); Christopher J. Danek, Santa Clara, CA (US)

(73) Assignee: Eclipse Surgical Technologies, Inc., Sunnyvale, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 126 days.

(21) Appl. No.: 08/942,874

(22) Filed: Oct. 2, 1997

Related U.S. Application Data

(63) Continuation-in-part of application No. 08/517,499, filed on Aug. 9, 1995.

(51) Int. Cl.⁷ .................................................. A61B 17/39
(52) U.S. Cl. ............................ 606/33; 607/101; 607/122
(58) Field of Search ................................. 606/33, 34, 37, 606/38, 122, 41; 604/114

(56) References Cited

U.S. PATENT DOCUMENTS

| | | |
|---|---|---|
| 4,211,230 * | 7/1980 | Woltosz . |
| 4,590,934 * | 5/1986 | Malis et al. . |
| 4,896,671 | 1/1990 | Cunningham et al. . |
| 5,056,517 | 10/1991 | Fenici . |
| 5,098,431 | 3/1992 | Rydell . |
| 5,125,926 | 6/1992 | Rudko et al. . |
| 5,172,699 | 12/1992 | Svenson et al. . |
| 5,188,635 | 2/1993 | Radtke . |
| 5,197,963 | 3/1993 | Parins . |
| 5,215,103 | 6/1993 | Desai . |
| 5,230,349 | 7/1993 | Langberg . |
| 5,231,995 | 8/1993 | Desai . |
| 5,257,635 | 11/1993 | Langberg . |
| 5,281,213 | 1/1994 | Milder et al. . |
| 5,281,218 | 1/1994 | Imran . |
| 5,295,484 | 3/1994 | Marcus et al. . |

(List continued on next page.)

FOREIGN PATENT DOCUMENTS

| | | |
|---|---|---|
| 0 428 812 | 3/1995 | (EP) . |
| 0 797 956 | 10/1997 | (EP) . |
| WO 94/10904 | 5/1994 | (WO) . |
| WO 94/21165 | 9/1994 | (WO) . |
| WO 94/21167 | 9/1994 | (WO) . |
| WO 94/21168 | 9/1994 | (WO) . |
| WO 96/26675 | 9/1996 | (WO) . |
| WO 96/35469 | 11/1996 | (WO) ............................ A61M/25/00 |

*Primary Examiner*—Linda C. M. Dvorak
*Assistant Examiner*—Roy Gibson
(74) *Attorney, Agent, or Firm*—Heller, Ehrman, White & McAuliffe LLP

(57) ABSTRACT

The invention is directed to an intracorporeal device for myocardial revascularization of a patient's heart tissue by at least one burst of RF energy over an interval of about 1 to about 500 msec, preferably about 30 to about 130 msec. The intracorporeal device has an elongated insulated, electrical conducting shaft with an uninsulated distal tip which is configured to emit RF energy. The uninsulated distal tip has a diameter of about 0.025 to about 0.2 inch, preferably about 0.04 to about 0.08 inch and a length of about 0.1 to about 5 mm, preferably about 1.5 to about 3.5 mm.

25 Claims, 4 Drawing Sheets

U.S. PATENT DOCUMENTS

| | | |
|---|---|---|
| 5,334,193 | 8/1994 | Nardella . |
| 5,370,644 | 12/1994 | Langberg . |
| 5,385,148 | 1/1995 | Lesh et al. . |
| 5,391,199 | 2/1995 | Ben-Haim . |
| 5,397,339 | 3/1995 | Desai . |
| 5,398,683 | 3/1995 | Edwards et al. . |
| 5,423,882 | 6/1995 | Jackman et al. . |
| 5,431,649 | 7/1995 | Mulier et al. . |
| 5,433,198 | 7/1995 | Desai . |
| 5,441,499 | 8/1995 | Fritzsch . |
| 5,476,495 | 12/1995 | Kordis et al. . |
| 5,480,422 | 1/1996 | Ben-Haim . |
| 5,487,757 | 1/1996 | Truckai et al. . |
| 5,492,119 | 2/1996 | Abrams . |
| 5,500,011 | 3/1996 | Desai . |
| 5,500,012 | 3/1996 | Brucker et al. . |
| 5,507,802 | 4/1996 | Imran . |
| 5,522,873 | 6/1996 | Jackman et al. . |
| 5,540,681 | 7/1996 | Strul et al. . |
| 5,545,200 | 8/1996 | West et al. . |
| 5,562,619 | 10/1996 | Mirarchi et al. . |
| 5,571,088 | 11/1996 | Lennox et al. . |
| 5,573,533 | 11/1996 | Strul . |
| 5,575,772 | 11/1996 | Lennox . |
| 5,578,007 | 11/1996 | Imran . |
| 5,579,764 | 12/1996 | Goldreyer . |
| 5,599,345 | 2/1997 | Edwards et al. . |
| 5,607,462 | 3/1997 | Imran . |
| 5,609,151 | 3/1997 | Mulier et al. . |
| 5,620,481 | 4/1997 | Desai et al. . |
| 5,626,575 | 5/1997 | Crenner . |
| 5,636,634 | 6/1997 | Kordis et al. . |
| 5,637,090 | 6/1997 | McGee et al. . |
| 5,657,755 | 8/1997 | Desai . |
| 5,658,278 | 8/1997 | Imran et al. . |
| 5,683,366 | 11/1997 | Eggers et al. . |
| 5,697,882 * | 12/1997 | Eggers et al. . |
| 5,722,975 | 3/1998 | Edwards et al. . |
| 5,725,524 | 3/1998 | Mulier et al. . |
| 5,728,144 | 3/1998 | Edwards et al. . |
| 5,741,249 | 4/1998 | Moss et al. . |
| 5,743,903 | 4/1998 | Stern et al. . |
| 5,843,019 * | 12/1998 | Eggers et al. . |

* cited by examiner

REVASCULARIZATION WITH RF ABLATION

RELATED APPLICATIONS

This application is a continuation-in-part of application Ser. No. 08/517,499, filed on Aug. 9, 1995, which is incorporated herein in its entirety.

BACKGROUND OF THE INVENTION

This invention is directed to the ablation of tissue in the wall of a patient's heart and particularly to form channels within the heart wall in order to perform transmyocardial revascularization (TMR), to deliver therapeutic or diagnostic agents to various locations in the patient's heart wall or for a variety of other utilities.

As presently used, TMR involves forming a plurality of channels in a ventricular wall of a patient's heart by means of laser energy. The first clinical trials of the TMR procedure using laser energy were performed by Mirhoseini et al. See for example the discussions in Lasers in General Surgery (Williams & Wilkins; 1989), pp 18 216–223. Other early disclosures of the TMR procedure are found in an article by Okada et al. in Kobe J. Med. Sci 32, 151–161, October 1986 and in U.S. Pat. No. 4,658,817 (Hardy). These early references describe intraoperative TMR procedures which require an opening in the chest wall and include formation of channels completely through the heart wall starting from the epicardium.

U.S. Pat. No. 5,554,152 which issued on Dec. 20, 1994 (Aita et al.), which is incorporated herein in its entirety, describes a system for TMR which is introduced through the chest wall either as an intraoperative procedure where the chest is opened up or as a minimally invasive procedure where the system is introduced into the patient's chest cavity through small openings in the chest by means of a thoroscope. In U.S. Pat. No. 5,389,096 (Aita et al.) a percutaneous TMR procedure is described wherein an elongated flexible laser based optical fiber device is introduced through the patient's peripheral arterial system, e.g. the femoral artery, and advanced through the aorta until the distal end of the device extends into the patient's left ventricle. Within the left ventricle, the distal end of the optical fiber device is directed toward a desired location on the patient's endocardium and urged against the endocardial surface while a laser beam is emitted from its distal end to form the channel.

The laser based revascularization procedure has been shown to be clinically beneficial to a variety of patients, particularly patients who were, for the most part, not suitable candidates for by-pass surgery or for minimally invasive procedures such as angioplasty or atherectomy. However, to date the equipment for laser based systems has been quite expensive. What has been needed is a system which is cheaper than but as clinically effective as laser based systems. The present invention satisfies these and other needs.

SUMMARY OF THE INVENTION

The present invention is directed to a method and system for the revascularization of a region of a patient's heart by ablating tissue in said region with emissions of radio frequency (RF) energy over discrete intervals and is particularly directed to the method and system to ablate tissue in the patient's heart wall to form channels therein by means of such RF energy.

In accordance with one embodiment of the invention, tissue is ablated within a patient's heart wall by means of one or more bursts of RF emissions over intervals of about one to about 500 msec and preferably about 30 to about 130 msec. An RF burst may comprise a continuous emission or discontinuous emission, i.e. be pulsatile, and, if pulsatile, may involve a plurality or train of pulses which may or may not be of the same width (duration), frequency or amplitude.

The RF emissions is preferably controlled so that heart tissue is exposed to the RF energy over a desired period and particularly over a period which will avoid interfering with the patient's heart beat, e.g. just after the R wave but before the T wave. One to about 10 bursts of RF energy may be required to effectively form the desired channel within the patient's heart wall and preferably one burst of RF emission is delivered per heart cycle. The RF energy source generally should have a peak power output of about 150 to about 500 watts, preferably about 200 to about 300 watts.

One presently preferred system for forming the channels in the patient's heart wall includes an RF energy transmitting member which has a proximal end, an elongated shaft insulated along a length thereof and an uninsulated distal tip configured to emit RF energy. The system is introduced into the patient and advanced within the patient until the uninsulated distal tip thereof is disposed adjacent to a surface of the patient's heart wall. At least one burst of RF energy from an RF energy source is transmitted through the RF energy transmitting member to the uninsulated distal tip thereof and from which transmitted RF energy transmitted is emitted to the surface of the heart wall in contact with said distal tip. The channel formed in the heart wall preferably has an aspect ratio, i.e. depth to width, of at least 1, preferably at least 2.

One embodiment of the invention involves a percutaneous approach wherein a flexible elongated RF energy delivery system is advanced through the patient's vasculature until a distal portion of the system enters a heart chamber such as the left ventricle. The RF energy delivery system is advanced so that the uninsulated distal tip thereof which emits RF energy contacts the interior surface of the heart wall which defines in part the heart chamber. At least one burst of RF energy is emitted from the uninsulated distal tip of the system into the patient's heart wall wherein tissue is ablated, resulting in the revascularization of the heart wall region.

Another embodiment of the invention involves a minimally invasive approach where a small incision is made in the patient's chest and with or without the benefit of a trocar sheath, an elongated RF energy transmitting system is advanced into the patient's chest cavity until the uninsulated distal tip of the RF transmitting system contacts the exterior of the patient's heart. One or more bursts of RF energy are emitted from the uninsulated distal tip so as to ablate tissue within the patient's heart wall causing the revascularization thereof as in the previously discussed embodiment of the invention. A similar procedure may be used in conjunction with an open chest procedure such as coronary by-pass surgery.

The RF energy transmitting system preferably includes an elongated electrical conducting shaft which is insulated along its length except for the distal tip thereof which is uninsulated and which is configured to contact the surface of the heart wall and to emit bursts of RF energy therefrom into adjacent tissue of the heart wall. The uninsulated distal tip has a diameter of about 0.025 to about 0.2 inch (0.64–5.1 mm), preferably about 0.04 to about 0.08 inch (1–2 mm) and a length of about 0.1 to about 5 mm, preferably about 1.5 to about 3.5 mm. The distal tip may be solid or hollow and may be relatively sharp or blunt. However, it should not be sharp enough to penetrate the tissue of the heart wall when pressed against the wall to maintain contact during the emission of RF energy bursts. The average power level should be about 50 to about 500 watts, preferably about 100 to about 300 watts. The frequency of the RF current should not be less than 100 khz and preferably is about 250 to about 500 khz.

The method and system of the invention effectively ablates tissue within the patient's heart wall to revascularize the ablated region and particularly can be used to form channels within the heart wall. These and other advantages of the invention will become more apparent from the following detailed description of the invention and the accompanying exemplary drawings.

DETAILED DESCRIPTION OF THE INVENTION

Figures 1, 2:
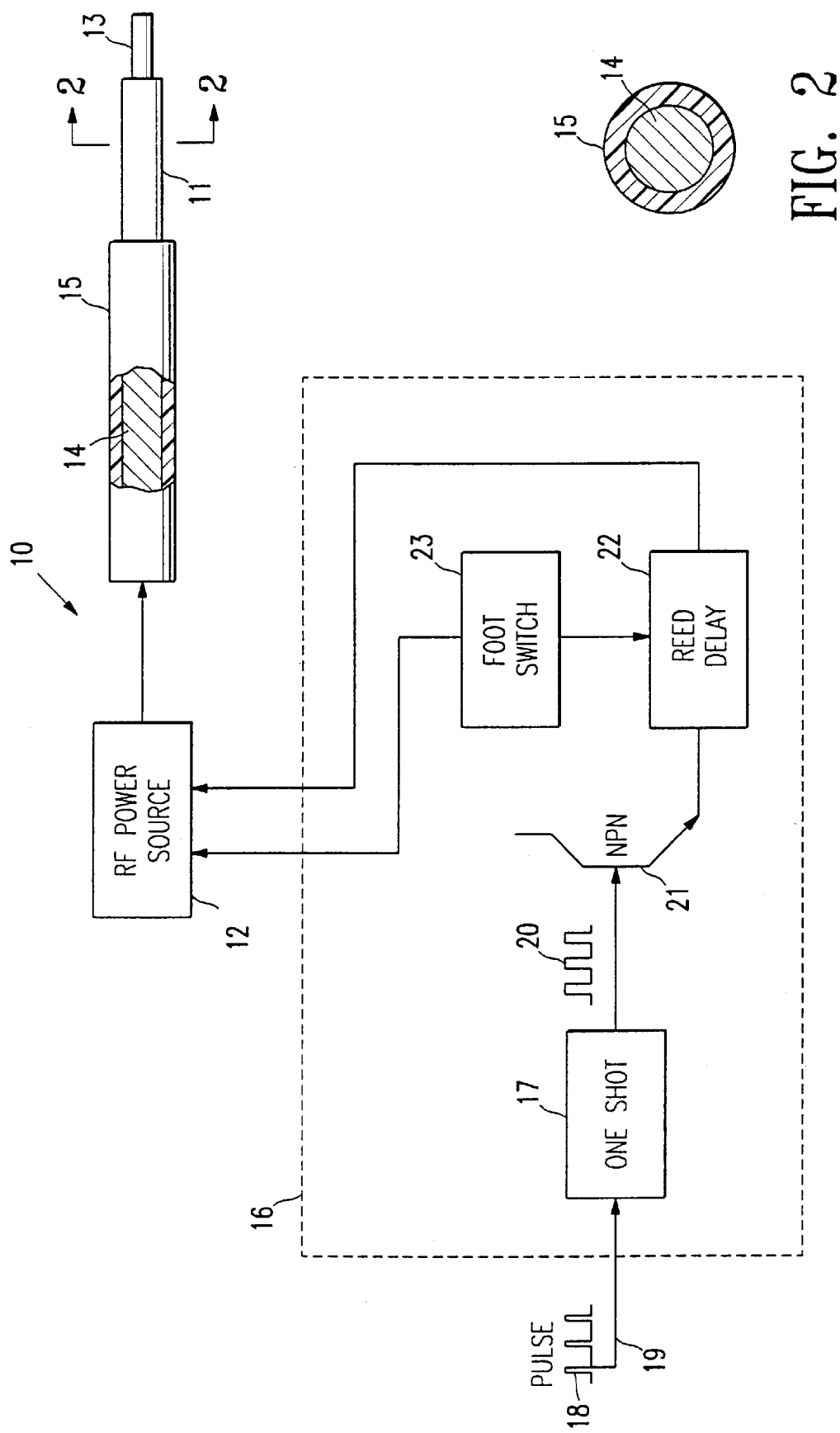
FIG. 1 is a schematic illustration of a system for ablating heart tissue which embodies features of the invention.
FIG. 2 is a transverse cross-section of the RF energy transmitting member system shown in FIG. 1 taken along the lines 2–2.

FIGS. 1 and 2 depict an RF ablation system 10 embodying features of the invention which includes an RF energy transmitting member 11 having a proximal end configured for electrical connection to a source 12 of RF energy and an uninsulated exposed distal end 13 which is configured to emit pulsed RF energy received from the source and transmitted through the electrical conductor. The RF energy transmitting member 11 includes an electrical conductor 14 which may be a single or multiple strand and an insulating jacket 15 formed of suitable insulating polymeric material. A suitable source of RF energy is the Excaliber RF Generator from Aspen Labs.

The output from the RF energy source 12 is pulsed by pulse-trigger system 16 which includes a one-shot 17, such as CD4047 sold by National Semiconductor, configured to receive trigger pulses 18 through electrical conductor 19 and generate in response a pulsed output signal 20 connected to a NPN transistor 21. The pulsed output signal 20 from the one-shot 17 actuates the transistor 21 for the duration of the output signal. The output of the transistor 21 is connected to reed relay 22 which is configured to close upon receiving the output from the transistor 21. The output of the reed relay 22 is connected in series to the foot switch 23. When the foot switch 23 is closed and reed relay 22 is closed, the RF source is actuated to emit RF energy for the duration of the output of the reed relay 22.

Figure 3:
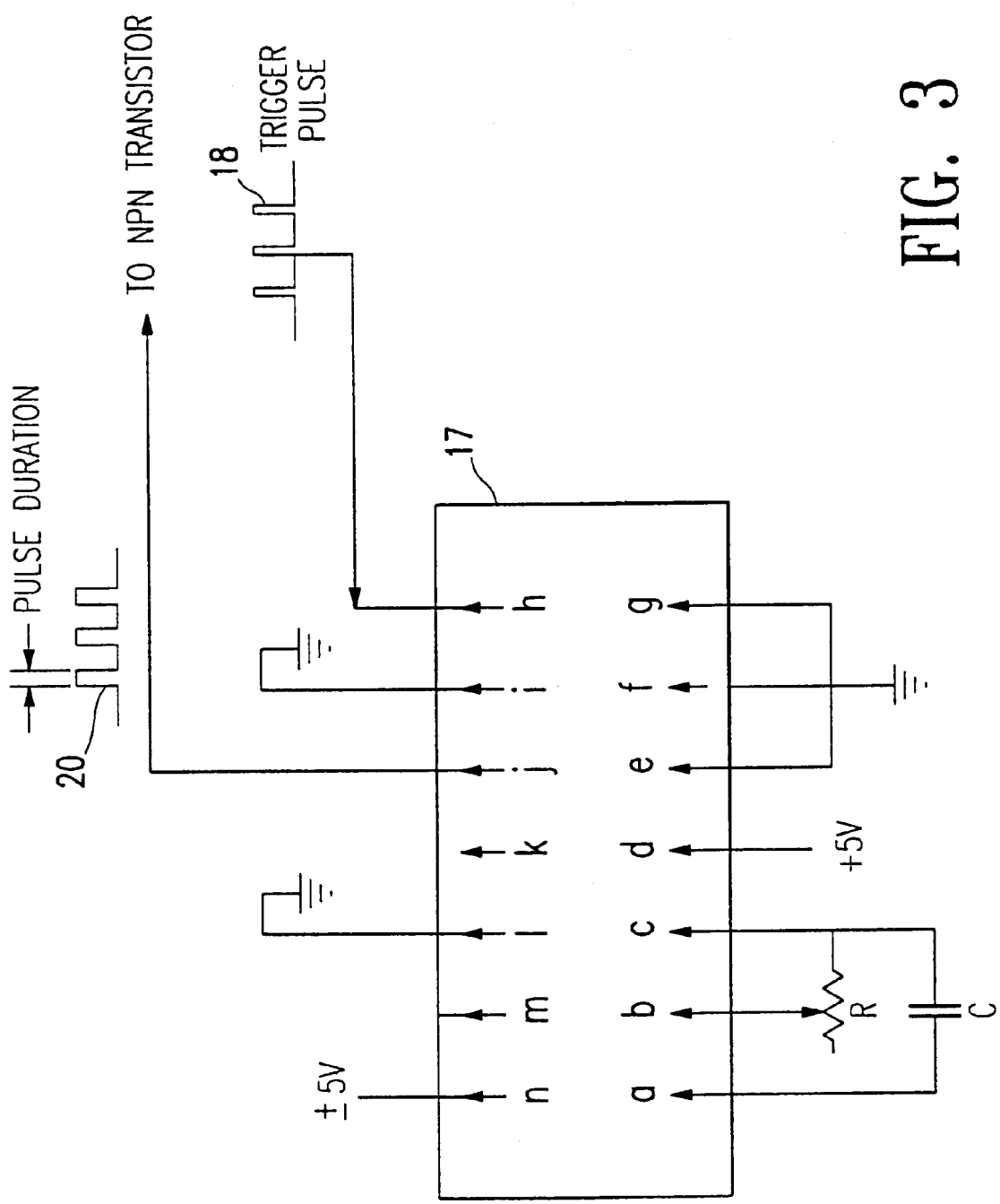
FIG. 3 is a schematic illustration of the one shot shown in FIG. 1.

FIG. 3 illustrates in more detail the one-shot shown in FIG. 1 which has 14 pins, identified as pins a–n in FIG. 3. The one-shot shown in FIG. 3 has the pins designated with letters a-n to avoid confusion with other reference numbers used herein. The one-shot model number CD4047 has these pins numbered 1–14. The trigger pulse 18 from an ECG unit is received by pin h and upon receipt of the trigger pulse and an on signal is emitted from pin j. The duration of the on signal from pin j is controlled by the resistance R and capacitance C from the RC circuit connected to pins a–c as shown. The resistance R can typically range from about 0.1 to about 1 meg ohm and the capacitance can typically range from about 0.08 to about 0.12 microfarads to control the duration of the pulses of output signal 20 from about 50 to about 300 msec.

Figure 4:
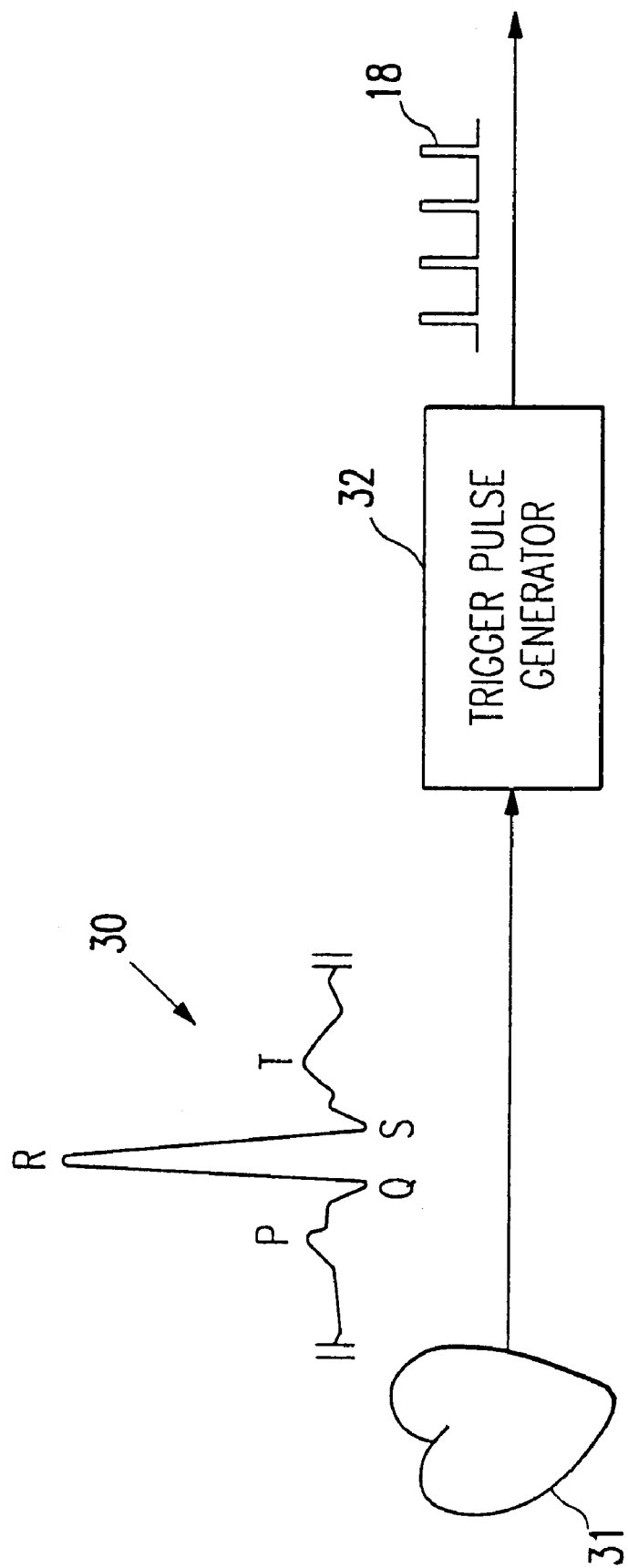
FIG. 4 is a schematic illustration of a system for generating trigger pulses based upon the patient's heart beat.

FIG. 4 schematically illustrates a system of generating trigger pulses 18 based upon the patient's heart cycle 30. The signals from the patients heart 31 are detected with a conventional ECG such as an IVY unit and detected signals are transmitted to a trigger generating system 32 which may also be contained in the IVY unit. The trigger pulse generating system 32 is preprogrammed to emit one or more trigger pulses 18 at a predetermined time between the R and the T wave of the heart cycle 30.

Figure 5:
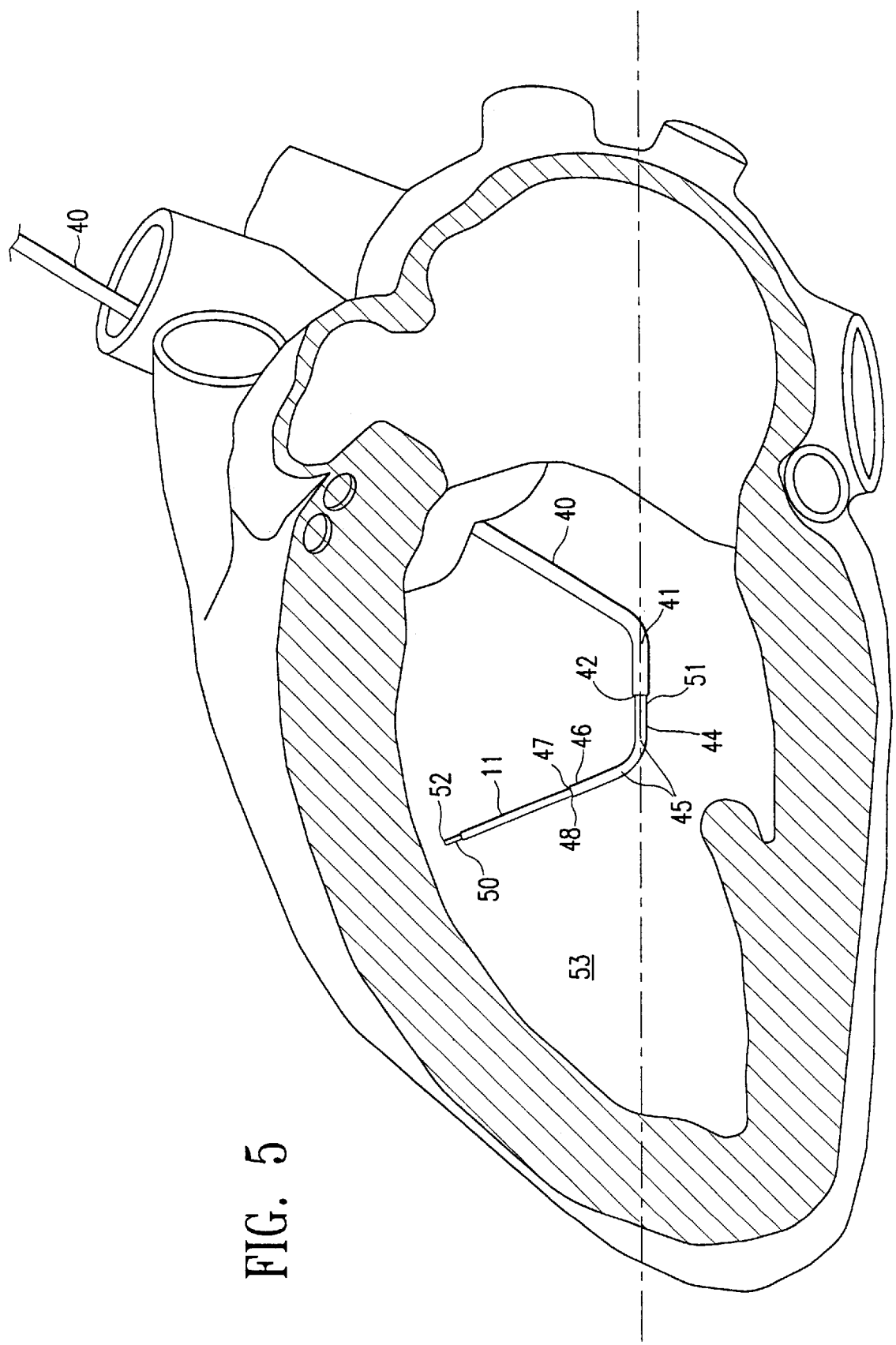
FIG. 5 is an elevational view of a delivery system for the RF ablation device for positioning the operative distal end thereof adjacent to the endocardium of a patient's heart wall.

Reference is made to FIG. 5 which illustrates a system for the percutaneous delivery of an RF ablation system which has an outer catheter 40, a shaped distal end 41, a port 42 in the distal end of the catheter and an inner lumen extending within the outer catheter to the port in the distal end. This system also includes an inner catheter 44 which is slidably and rotatably disposed within the inner lumen of the outer catheter 40 and which has a shaped distal section 45, a distal end 46, a port 47 in the distal end of the inner catheter and an inner lumen 48 extending therein to the port in the distal end. An RF ablation device 50 is slidably disposed within the inner lumen of inner catheter 44. The distal section 45 of the inner catheter 44 is at an angle with respect to the main shaft section 51 of the inner catheter to orient the RF ablation device 50 extending out the distal end of the inner catheter. In this manner the disposition of the distal end 52 of the RF ablation device 50 can be controlled by raising and lowering and rotation of the RF ablation device within the inner lumen of the inner catheter 44 and the inner catheter within the inner lumen of the outer catheter 40. The distal end 52 of the RF ablation device 50 is thus pointed in a desired direction to the endocardium defining the left ventricle 53. Longitudinal and rotational movement of the inner catheter 44 provides access to a large region of the endocardium.

EXAMPLE

Eighteen channels were made in the heart of a live, anesthetized medium size dog by means of pulsed RF energy. The wattage and the size and type of distal tip of the RF delivery system were varied to determine the nature of the channels formed which result from such variations. The results are set forth in the table below.

| WATTAGE | DISTAL TIP TYPE | UNINSULATED LENGTH | PULSE DURATION | NO. OF PULSES |
| --- | --- | --- | --- | --- |
| 200 watts | Hollow | 0.05 inch | 100 msec | 6 |
| 200 watts | Hollow | 0.05 inch | 100 msec | 5 |
| 200 watts | Hollow | 0.05 inch | 100 msec | 5 |
| 200 watts | Hollow | 0.05 inch | 100 msec | 6 |
| 200 watts | Hollow | 0.05 inch | 100 msec | 5 |
| 200 watts | Hollow | 0.05 inch | 100 msec | 5 |
| 300 watts | Hollow | 0.05 inch | 100 msec | 3 |
| 300 watts | Hollow | 0.05 inch | 100 msec | 4 |
| 300 watts | Hollow | 0.05 inch | 100 msec | 4 |
| 300 watts | Hollow | 0.05 inch | 100 msec | 5 |
| 300 watts | Hollow | 0.05 inch | 100 msec | 4 |
| 300 watts | Hollow | 0.05 inch | 100 msec | 5 |
| 300 watts | Solid | 0.15 inch | 100 msec | 4 |

-continued

| WATTAGE | DISTAL TIP TYPE | UNINSULATED LENGTH | PULSE DURATION | NO. OF PULSES |
|---|---|---|---|---|
| 300 watts | Solid | 0.15 inch | 100 msec | 5 |
| 300 watts | Solid | 0.15 inch | 100 msec | 6 |
| 300 watts | Solid | 0.15 inch | 100 msec | 7 |
| 300 watts | Solid | 0.15 inch | 100 msec | 5 |
| 300 watts | Solid | 0.15 inch | 100 msec | 5 |

Those skilled in the art will recognize that various changes can be made to the invention without departing from the scope thereof.

What is claimed is:

1. A method of forming a channel in a patient's heart wall, comprising:
   a) providing an elongated RF energy transmitting device having proximal and distal ends and which includes an elongated insulated electrical conductor and an uninsulated distal tip having a length of about 1.5 to 3.5mm configured to emit RF energy;
   b) introducing the elongated RF energy transmitting device into the patient and advancing the elongated RF energy transmitting device therein until the uninsulated distal tip thereof is disposed adjacent to a surface of the patient's heart wall; and
   c) emitting one or more bursts of pulsed RF energy from the uninsulated distal tip of the RF energy transmitting device over at least one interval from about 1 to about 500 msec to form a channel within the heart wall by ablating tissue therein.

2. The method of claim 1 wherein one or more bursts of RF energy are emitted from the distal tip over an interval of about 30 to about 130 msec.

3. The method of claim 1 wherein the channel is formed during a single interval.

4. The method of claim 1 wherein the individual pulses have durations of at least about 1 msec.

5. The method of claim 1 wherein from about 2 to about 10 bursts of pulsed RF energy are emitted from the uninsulated distal tip to form the channel.

6. A method of revascularizing a desired region of a patient's heart wall, comprising:
   a) providing an elongated flexible RF energy transmitting device having proximal and distal ends and which includes an uninsulated distal tip having a length of about 1.5 to about 3.5 mm configured to emit RF energy;
   b) introducing the elongated flexible RF energy transmitting device into the patient's vasculature and advancing the elongated flexible RF energy transmitting device therein until the uninsulated distal tip thereof is disposed adjacent to and in contact with a surface of the patient's heart wall; and
   c) delivering pulsed RD energy from a source thereof through the RF energy transmitting member to said uninsulated distal tip; and
   d) emitting at least one burst of pulsed RF energy from the uninsulated distal tip of the elongated flexible RF energy transmitting device over an interval of about 1 to about 500 msec to ablate tissue in the desired region of the patient's heart wall.

7. The method of claim 6 wherein the RF energy source has a peak power output of about 200 to about 500 watts.

8. A percutaneous method of revascularizing a desired region of a patient's heart wall, comprising:
   providing an elongated flexible RF energy transmitting device having proximal and distal ends and which includes an elongated insulated electrical conducting member and an uninsulated distal tip having a length of about 1.5 to about 3.5 mm configured to emit RF energy;
   b) introducing the elongated flexible RF energy transmitting device into the patient's vasculature and advancing said device therein until the uninsulated distal tip thereof is disposed adjacent to and in contact with a surface of the patient's heart wall;
   c) delivering at least one burst of pulsed RF energy over an interval of about 1 to about 500 msec from a source thereof through the RF energy transmitting device to the uninsulated distal tip thereof; and
   d) emitting at least one transmitted burst of pulsed RF energy from the uninsulated distal tip to ablate tissue in the desired region of the patient's heart wall.

9. The method of claim 8 wherein a channel is formed by a tissue ablation.

10. The method of claim 8 wherein each individual pulse of RF energy has a duration of at least one msec.

11. The method of claim 8 wherein the RF source has a peak power output of about 200 to about 500 watts.

12. A system for ablating tissue in a wall of a patient's heart with one or more bursts of pulsed RF energy, comprising:
   a) a source for RF energy; and
   b) a control unit which is operatively connected to receive trigger pulses from a source thereof and which emits control signals to the source of RF energy upon receipt of trigger signals to activate the RF energy source to emit at least one burst of pulsed RF energy based upon a trigger pulse receiver; and
   c) an RF energy transmitting member having a proximal end which is configured to receive RF energy from the source, an elongated shaft configured to transmit RF energy received from said source and an uninsulated distal tip having a length of about 1.5 to about 3.5 mm configured to emit transmitted RF energy to a patient's heart wall to ablate tissue therein.

13. The system of claim 12 wherein control signals from the control unit control the duration of at least one burst of RF energy.

14. The system of claim 12 including a subsystem to sense the patient's heart beat and to emit at least one trigger pulse during a desired portion of the patient's heart cycle to generate and deliver at least one burst of RF energy.

15. An elongated intracorporeal device to form channels within a wall of a patient's heart, comprising:
   an elongated shaft having an electrical conducting member with a distal end, a proximal end and an uninsulated distal tip with a length of about 1.5 to about 3.5 mm and with a diameter of about 0.025 to about 0.20 inch configured to emit pulses of RF energy; and
   an RF energy source configured to emit bursts of pulsed RF energy of about 1 to about 500 msec electrically coupled to the proximal end of the electrical conducting member.

16. The elongated intracorporeal device of claim 15 wherein the uninsulated distal tip has a length of about 0.1 to about 5 mm.

17. A method of revascularizing a desired region of a patient's heart wall, comprising:
   a) providing an RF energy transmitting device having proximal end, an elongated insulated shaft and an uninsulated distal tip having a length of about 1.5 to about 3.5 mm configured to emit RF energy;

c) during a desired period of the patient's heart cycle, emitting at least one burst of pulsed RF energy from the uninsulated distal tip of the elongated flexible RF energy transmitting device as to ablate tissue in the desired region of the patient's heart wall to revascularize the desired region.

18. The method of claim 17 wherein the pulsatile RF energy emission is a train of pulses.

19. The method of claim 17 wherein at least one burst of RF energy is emitted from said uninsulated distal tip over an interval of about 1 to about 500 msec.

20. The method of claim 17 wherein at least one burst of RF energy is emitted from said uninsulated distal tip over an interval of about 30 to about 150 msec.

21. A method of forming a channel in a desired region of a patient's heart wall, comprising:

a) providing an RF energy transmitting member having a proximal end, an elongated insulated shaft and an uninsulated distal tip having a length of about 1.5 to about 3.5 mm configured to emit RF energy;

b) introducing at least a distal portion of the elongated RF energy transmitting member into the patient until the uninsulated distal tip thereof is disposed adjacent to and in contact with a surface of the patient's heart wall; and c) emitting at least one burst of pulsed RF energy from the uninsulated distal tip over an interval of about 1 to about 500 msec to form a channel in the desired region of the patient's heart wall by ablating tissue therein.

22. The method of claim 19 wherein at least one burst of RF energy is emitted from said uninsulated distal tip over an interval of about 30 to about 150 msec.

23. The method of claim 22 wherein the desired period of the patient's heart cycle is between the R wave and the T wave of the patient's heart cycle.

24. The method of claim 23 including detecting a desired period of the patient's heart cycle; and emitting said at least one burst of pulsed RF energy from the uninsulated distal tip during the detected desired period.

25. The method of claim 24 wherein the desired period of the patient's heart cycle is between the R wave and the T wave of the patient's heart cycle.

* * * * *

UNITED STATES PATENT AND TRADEMARK OFFICE
CERTIFICATE OF CORRECTION

PATENT NO. : 6,267,757 B1
DATED : July 31, 2001
INVENTOR(S) : Aita et al.

It is certified that error appears in the above-identified patent and that said Letters Patent is hereby corrected as shown below:

Column 1,
Line 22, delete "18".

Column 5,
Line 56, "RD" should read -- RF --.

Column 6,
Line 1, "providing" should read -- a) providing --;
Line 20, "a" should read -- said --;
Line 61, "length" should read -- diameter --; and "0.1" should read -- 0.04 --;
Line 62, "5 mm" should read -- 0.08 inch --.

Column 7,
Line 3, insert the following paragraph,
b) introducing at least a distal portion of the RF energy transmitting device into the patient and advancing said device until the uninsulated distal tip thereof is disposed adjacent to and in contact with a surface of the patient's heart wall; and Column 8,
Line 9, cancel beginning with "22. The method" to and including "150 msec."
in line 11, and insert the following claim:
22. The method of claim 21 including detecting a desired period of the patient's heart cycle; and emitting said at least one burst of pulsed RF energy from the uninsulated distal tip during the detected desired period.

UNITED STATES PATENT AND TRADEMARK OFFICE
CERTIFICATE OF CORRECTION

PATENT NO. : 6,267,757 B1
DATED : July 31, 2001
INVENTOR(S) : Aita et al.

It is certified that error appears in the above-identified patent and that said Letters Patent is hereby corrected as shown below:

Cont'd,
Column 8,
Line 15, cancel beginning with "24. The method" to and including "heart cycle." in line 21.

Signed and Sealed this

Twenty-first Day of May, 2002

Attest:

Attesting Officer

JAMES E. ROGAN
Director of the United States Patent and Trademark Office